(12) United States Patent
Mendelson et al.

(10) Patent No.: US 9,155,637 B2
(45) Date of Patent: Oct. 13, 2015

(54) BIOABSORBABLE STENT WITH HYDROTHERMAL CONVERSION FILM AND COATING

(71) Applicant: Medtronic Vascular, Inc., Santa Rosa, CA (US)

(72) Inventors: Jill P. Mendelson, San Francisco, CA (US); Ya Guo, Santa Rosa, CA (US); Christopher W. Storment, Sonoma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 25 days.

(21) Appl. No.: 13/800,121

(22) Filed: Mar. 13, 2013

(65) Prior Publication Data
US 2014/0277396 A1    Sep. 18, 2014

(51) Int. Cl.
| A61F 2/82 | (2013.01) |
| A61L 31/02 | (2006.01) |
| A61L 31/10 | (2006.01) |
| A61L 31/14 | (2006.01) |

(52) U.S. Cl.
CPC ............ *A61F 2/82* (2013.01); *A61L 31/022* (2013.01); *A61L 31/10* (2013.01); *A61L 31/14* (2013.01); *A61L 31/148* (2013.01)

(58) Field of Classification Search
CPC .................................................. A61F 2/82
USPC ................................. 623/1.11–1.48
See application file for complete search history.

(56) References Cited

U.S. PATENT DOCUMENTS

| 8,382,823 B2* | 2/2013 | Kim et al. ............. 623/1.44 |
| 2009/0131540 A1* | 5/2009 | Hiromoto et al. ....... 514/769 |
| 2010/0136506 A1* | 6/2010 | Park ..................... 433/201.1 |
| 2010/0191324 A1 | 7/2010 | Klocke |
| 2010/0279179 A1* | 11/2010 | Farrow et al. ........... 429/401 |
| 2011/0189377 A1* | 8/2011 | Atanasoska et al. ..... 427/2.1 |
| 2011/0238153 A1* | 9/2011 | Atanasoska et al. ... 623/1.15 |
| 2012/0041540 A1* | 2/2012 | Shobayashi et al. ... 623/1.15 |
| 2012/0059455 A1* | 3/2012 | Weber et al. ............ 623/1.42 |
| 2013/0078476 A1* | 3/2013 | Riman et al. ............ 428/469 |
| 2013/0190888 A1* | 7/2013 | Novak Krmpotic et al. 623/23.6 |
| 2013/0226310 A1* | 8/2013 | Schwartz et al. ...... 623/23.56 |
| 2014/0030310 A1* | 1/2014 | Bayer et al. ............. 424/423 |
| 2014/0079741 A1* | 3/2014 | Bink et al. ............... 424/400 |
| 2014/0093417 A1* | 4/2014 | Liu et al. ................. 420/411 |
| 2014/0236284 A1* | 8/2014 | Stinson et al. .......... 623/1.38 |
| 2014/0249614 A1* | 9/2014 | Levi et al. ............... 623/1.11 |

FOREIGN PATENT DOCUMENTS

EP    1997522    12/2008

OTHER PUBLICATIONS

PCT/US2014/017485, PCT Search Report and Written Opinion, mailed Apr. 29, 2014.

* cited by examiner

*Primary Examiner* — Suzette J Gherbi

(57) ABSTRACT

A stent includes a bioabsorbable metal, a hydrothermal conversion film covering the bioabsorbable metal, and a coating covering the hydrothermal conversion film. A method for manufacturing a stent includes forming a stent body comprising a bioabsorbable metal, forming a hydrothermal conversion film over surfaces of the stent body, and coating the hydrothermal conversion film with an overcoat.

24 Claims, 8 Drawing Sheets

BIOABSORBABLE STENT WITH HYDROTHERMAL CONVERSION FILM AND COATING

FIELD

The present invention is related to bioabsorbable stents that include a hydrothermal conversion film and coating.

BACKGROUND

A stent is typically a hollow, generally cylindrical device that is deployed in a body lumen from a radially contracted configuration into a radially expanded configuration, which allows it to contact and support a vessel wall. A plastically deformable stent may be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s) or strip(s) of material, may be cut from a tube, or may be cut from a sheet of material and then rolled into a tube-like structure. Magnesium alloys are being investigated as a material for a bioabsorbable stent due to their biocompatibility and ability to degrade in vivo. A three to six month period of mechanical integrity is desired, with complete degradation within twelve months. Magnesium alloys generally corrode too quickly to be used bare. Many methods that may be used to slow corrosion, such as anodization, have not been effective and are also typically work/time intensive processes.

Hydrothermal treatment is one option to slow corrosion of magnesium alloy stents. During the hydrothermal process, a hydrothermal conversion film (hydrothermal film) is formed on the surface of the metal sample and acts as a barrier to slow down the rate of corrosion of the metal sample. Although hydrothermal films have been used for various applications in the past for relatively large metal samples with simple geometries, hydrothermal films have not been used on complex geometries with high surface area to volume ratios, such as stents.

The hydrothermal films reported in the literature typically have large thicknesses and their corrosion prevention effectiveness has been demonstrated under static conditions. Hydrothermal films have not been considered to be applicable to stents, where a very thin layer of film is desired due to the small size of a stent, as well as the need to withstand bending and other dynamic conditions. Hydrothermal films are also not typically utilized for samples that must withstand corrosion while implanted in the human body. New coating technologies are needed to delay magnesium corrosion for up to three months, as well as to provide a more uniform corrosion throughout the stent.

SUMMARY

It is desirable to provide a bioabsorbable stent for which the rate of corrosion may be controlled, and a method of manufacturing such a stent.

According to an aspect of the invention, there is provided a stent that includes a bioabsorbable metal, a hydrothermal conversion film covering the bioabsorbable metal, and a coating covering the hydrothermal conversion film.

In an embodiment, the bioabsorbable metal includes a magnesium alloy. In an embodiment, the magnesium alloy includes 90-98 weight % magnesium, 0-6 weight % aluminum, 0-2 weight % zinc, and 0-3% rare earth metal. In an embodiment, the magnesium alloy includes 94 weight % magnesium, 4 weight % aluminum, and 2% rare earth metal.

In an embodiment, the hydrothermal conversion film includes at least one component selected from the group consisting of: magnesium hydroxide and magnesium oxide.

In an embodiment, the coating includes a non-biodegradable polymer. In an embodiment, the non-biodegradable polymer is selected from the group consisting of: parylene, polymethacrylates, and polyurethane.

In an embodiment, the coating includes a biodegradable polymer. In an embodiment, the biodegradable polymer is a homopolymer or a copolymer including polylactide, poly (lactide-co-caprolactone), poly(DL-lactide-co-caprolactone), or poly(trimethylene carbonate).

In an embodiment, the coating includes a biodegradable atomic layer deposition coating.

In an embodiment, the biodegradable atomic layer deposition coating includes zircol nanolaminates, alternating alumina-zircol nanolaminates, or alternating zirconia-zircol nanolaminates.

In an embodiment, the hydrothermal conversion film encapsulates the bioabsorbable metal.

In an embodiment, the coating encapsulates the hydrothermal conversion film and the bioabsorbable metal.

In an embodiment, the coating includes a therapeutic substance.

According to an aspect of the invention, there is provided a method for manufacturing a stent. The method includes forming a stent body comprising a bioabsorbable metal, forming a hydrothermal conversion film over surfaces of the stent body, and coating the hydrothermal conversion film with a polymer overcoat.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
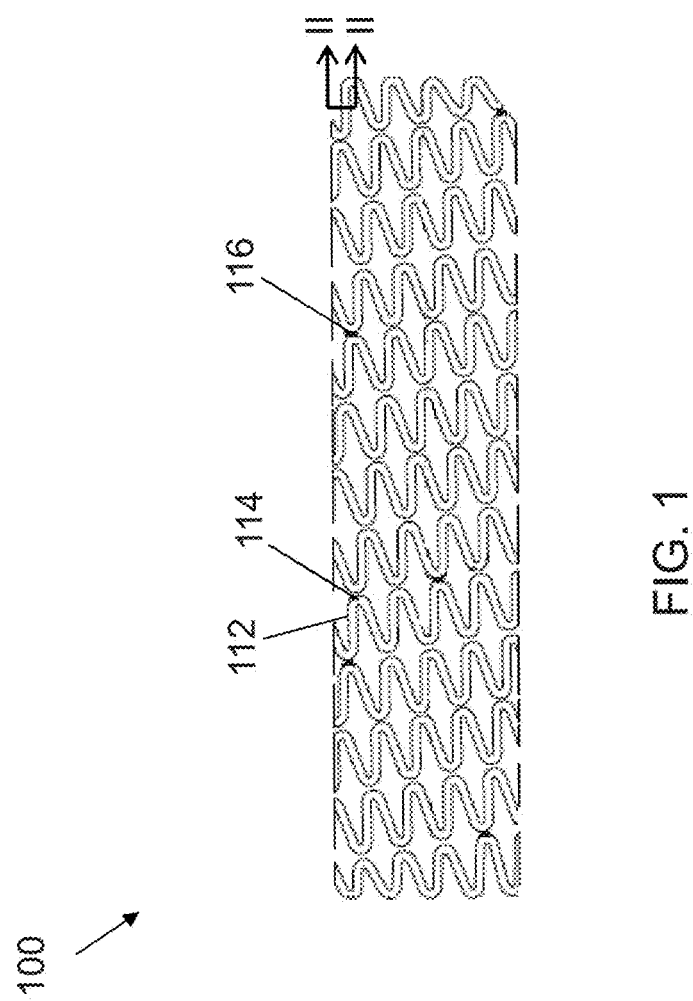
FIG. 1 schematically illustrates a stent in accordance with an embodiment of the invention.

FIG. 1 depicts a stent 100 according to an embodiment of the invention. As illustrated, the stent 100 includes a plurality of struts 112 and a plurality of crowns or turns 114, with each crown or turn 114 connecting a pair of adjacent struts 112. The stent 100 may be formed from a tube or wire using methods known in the art. For example, if a tube is used to form the stent 100, the tube may be cut with a laser or etched with the pattern of the stent 100 by known methods. If a wire is used to form the stent 100, the wire may be formed into a generally sinusoidal waveform, and wrapped around a mandrel or rod. Select neighboring crowns may be fused together at connection points 116, and the ends of the wire may be cut by a laser where the stent terminates.

Figure 2:
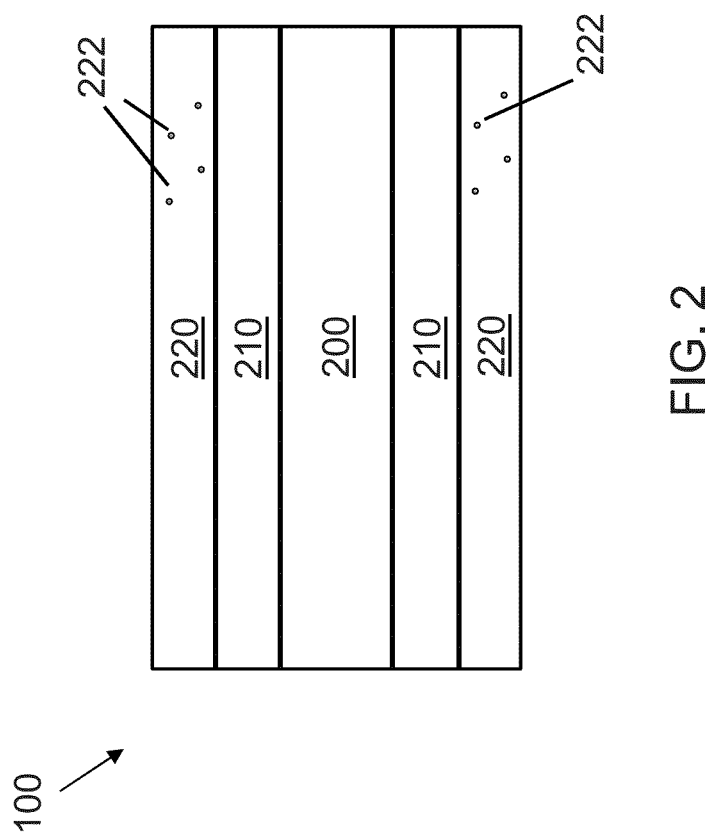
FIG. 2 is a schematic cross-section of the stent of FIG. 1, taken along line II-II.

FIG. 2 illustrates a schematic cross-section of the stent 100 taken along line II-II of FIG. 1. As illustrated, the stent 100 includes a stent body 200, which provides the structure of the stent 100, a first coating 210 in contact with the stent body 200, and a second coating 220 in contact with the first coating. The stent body 200 may be formed from a biodegradable metal, such as a magnesium alloy. In an embodiment, the magnesium alloy may include 90-98 weight % magnesium, 0-6 weight % aluminum, 0-2 weight % zinc, and 0-3% rare earth metal(s). In an embodiment, the magnesium alloy may be AE42, which includes 94 weight % magnesium, 4 weight % aluminum, and 2 weight % rare earth metal(s).

The first coating 210 may be a hydrothermal conversion film, which may be created through embodiments of the invention discussed in further detail below. The hydrothermal conversion film may contain an oxide or a salt, for example. In an embodiment, the hydrothermal film may include hydrated magnesium oxide or magnesium hydroxide. In an embodiment, the hydrothermal film may include magnesium phosphate and/or other magnesium salts, depending on the formulation used during the hydrothermal process, as described in further detail below.

In an embodiment, one or more additives may also be added into the formulation of the solution used during the hydrothermal process for incorporation into the film to improve the properties of the first coating 210. The additive(s) may include organic acids, surfactants, etc. In an embodiment, the additive(s) may include stearic acid, lauric acid, octadecylphosphonic acid, or tannic acid. In an embodiment, an organic solvent based formulation may be used to increase solubility of organic additives and promote better incorporation into the hydrothermal conversion film.

The second coating 220 may include a polymer. In an embodiment, the polymer may be a degradable polymer. The degradable polymer may be polylactide, poly(lactide-co-caprolactone), poly(DL-lactide-co-caprolactone), poly(trimethylene carbonate), their copolymers, etc. In an embodiment, the polymer may be a nondegradable or stable polymer, and may be parylene, polymethacrylates, polyurethane, etc. In the embodiment illustrated in FIG. 2, the second coating 220 includes a therapeutic substance or agent 222 that is configured to be released from or eluted by the second coating 220 after the stent 100 has been implanted at the target location. Including the therapeutic substance or agent 222 in the second coating is considered to be optional. For example, if the stent 100 is intended to be a drug eluting stent, the second coating 220 may include the therapeutic substance or agent 222. If the stent 100 is not intended to be a drug eluting stent, the second coating 220 may not include the therapeutic substance or agent 222. The illustrated embodiment is not intended to be limiting in any way.

The therapeutic substance or agent 222 may include, but is not limited to antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., TAXOTERE® from Aventis S. A., Frankfurt, Germany), methotrexate, azathioprine, vincristine, vinblastine, fluorouracil, doxorubicin hydrochloride (e.g., ADRIAMYCIN® from Pharmacia & Upjohn, Peapack N.J.), and mitomycin (e.g., MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., PRINIVIL® and PRINZIDE® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include nitric oxide, alpha-interferon, genetically engineered epithelial cells, and dexamethasone. In other examples, the therapeutic substance is a radioactive isotope for implantable device usage in radiotherapeutic procedures. Examples of radioactive isotopes include, but are not limited to phosphorus ($P^{32}$), palladium ($Pd^{103}$), cesium ($Cs^{131}$), Iridium ($Ir^{192}$) and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances or agents are equally applicable for use with the disclosed methods and compositions.

Examples

Biodegradable hydrothermal conversion films comprising magnesium oxide were formed with thicknesses and compositions that were altered by adjusting the soaking solution concentration and composition, time, and temperature. Although embodiments of the present invention provide for the hydrothermal conversion films of up to 20 μm thick to be created, thinner films (i.e. <2 μm in thickness) are desirable to minimize film cracking in view of the bending and other dynamic conditions that the stents are subjected to. The hydrothermal conversion films in accordance with embodiments of the invention may be formed in a batch process that is superior to anodization process. The hydrothermal conversion films incorporate the insoluble particulates of the magnesium alloy used to form the stent body 200. The hydrothermal process typically results in a uniform film across the stent even with the complex geometry.

A 0.25M solution of trisodium phosphate dodecahydrate ($Na_3PO_4$) was used as the aqueous soaking solution in a Parr mini bench top stirred reactor, with the stent bodies held separate from each other on a fixture. Other solutions that may be utilized include sodium hydroxide (NaOH), and concentrations other than 0.25M may also be used. A stirrer within the Teflon-lined reactor was used to keep the temperature uniform throughout the reactor. The stent bodies were submerged in the aqueous solution, and the reactor was sealed and heated to 90-160° C., depending on the desired thickness. The temperature in the reactor was monitored through a thermocouple and the pressure in the reactor was monitored with a pressure gauge. After the stent bodies were heated in the reactor for a suitable amount of time, the heater was turned off and removed from the reactor to allow the reactor to cool to a temperature between 50-60° C. The stents bodies were then taken out of the reactor, rinsed with deionized water and ethanol, and dried.

In an embodiment, the solution for the hydrothermal reactor may include 0.1-0.4M $Na_3PO_4$, the temperature of the reactor may be set to 90° C., and the stent bodies may be heated in the reactor for 20-24 hours. In an embodiment, the solution for the hydrothermal reactor may include 5.66 wt % NaOH, the temperature of the reactor may be set to 90-160° C., and the stent bodies may be heated in the reactor for 18-96 hours.

In an embodiment, the solution for the hydrothermal reactor may include a silicate solution that includes, for example, KOH and $K_2SiO_3$. Additives may also be included within the aqueous solution, such as stearic or lauric acid. These additives should become incorporated into the film and may fill in any cracks that form in the film, which may prevent film cracking from affecting the corrosion resistance of the film. In an embodiment, the solution for the hydrothermal reactor may also include 1-5 g of at least one of stearic acid, lauric acid, tannic acid, 4-(4-Nitrophenylazo)resorcinol (i.e. magnesium reagent II), and octadecylphosphonic acid.

Table I lists the film thicknesses of hydrothermal conversion films that were formed on stent bodies formed from AE42, along with the type of solution, temperature, and time the stent bodies were subjected to in the hydrothermal reactor using the process described above.

TABLE I

Hydrothermal Conversion Film Thicknesses as a Function of Type of Solution, Temperature, and Time

| Example | Solution | Temperature | Time | Film Thickness |
|---|---|---|---|---|
| 1 | 0.25M $Na_3PO_4$ | 90° C. | 20 hours | 1-2 μm |
| 2 | 0.25M $Na_3PO_4$ | 90° C. | 22 hours | 1.2-2.5 μm |
| 3 | 0.25M $Na_3PO_4$ | 90° C. | 24 hours | 2-3 μm |
| 4 | 0.25M $Na_3PO_4$ | 110° C. | 20 hours | 5.5-6.5 μm |

TABLE I-continued

Hydrothermal Conversion Film Thicknesses as a Function of Type of Solution, Temperature, and Time

| Example | Solution | Temperature | Time | Film Thickness |
|---|---|---|---|---|
| 5 | 5.66 wt % NaOH | 100° C. | 18 hours | 2.5-3 μm |
| 6 | 5.66 wt % NaOH | 100° C. | 24 hours | 7-8 μm |
| 7 | 5.66 wt % NaOH | 100° C. | 96 hours | 9-13 μm |

Figure 3:
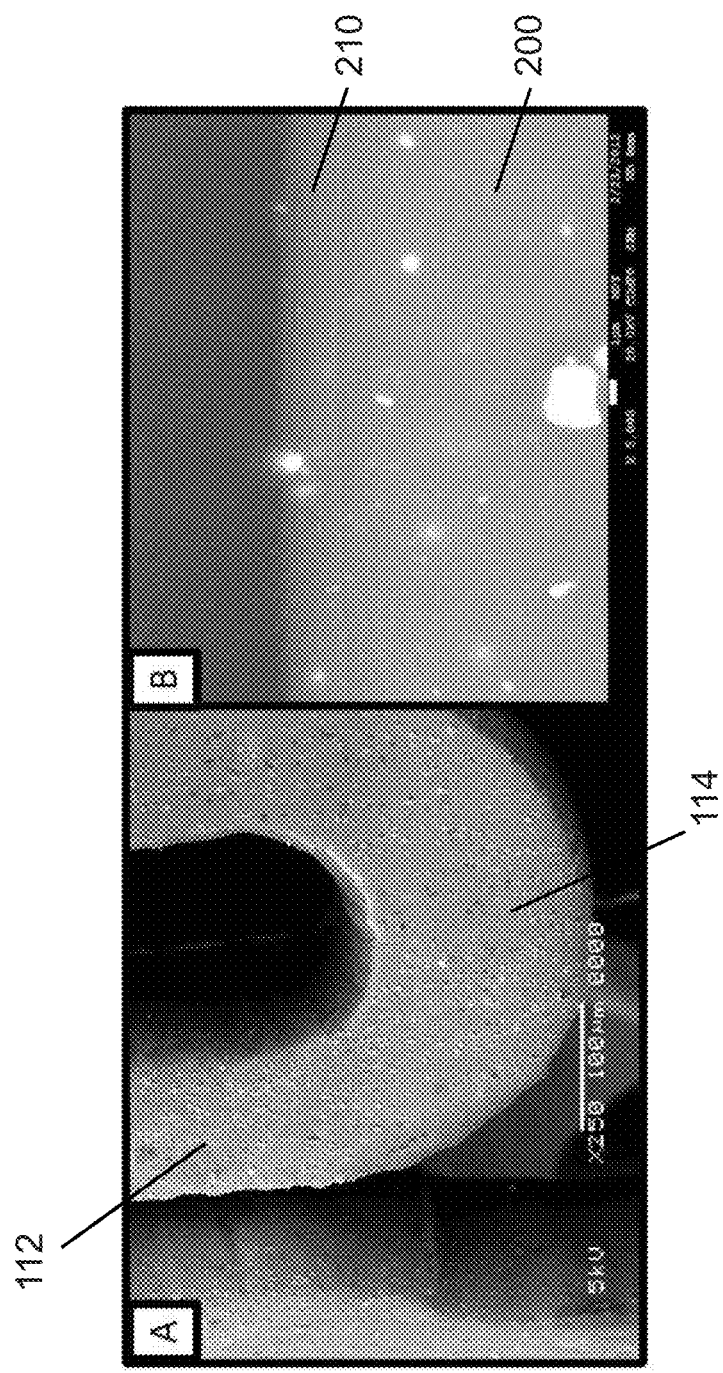
FIG. 3A is a scanning electron micrograph of a hydrothermal conversion film on a magnesium alloy stent body, according to an embodiment of the invention.
FIG. 3B is a cross-section of the stent of FIG. 3A showing the hydrothermal conversion film has a thickness of about 2 μm.
Figure 4:
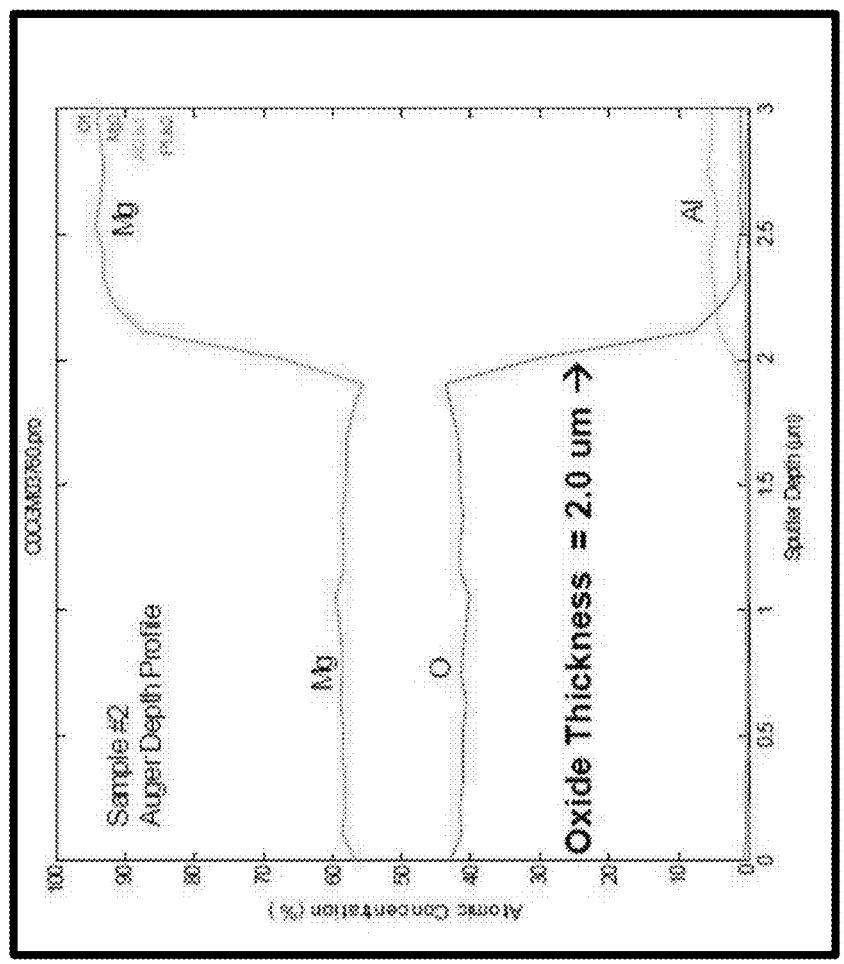
FIG. 4 is an Auger Depth Profile of the hydrothermal conversion film of FIGS. 3A and 3B.

FIG. 3A is a scanning electron micrograph (SEM) of Example 2, i.e. a hydrothermal conversion film on a magnesium alloy (AE42) stent body that was formed in an aqueous solution with 0.25M $Na_3PO_4$ at a temperature of 90° C. for 22 hours. FIG. 3B is a cross-section of the stent of FIG. 3A showing the hydrothermal film to have a thickness of about 2 μm, and FIG. 4 illustrates the Auger Depth Profile of Example 2.

Figure 5:
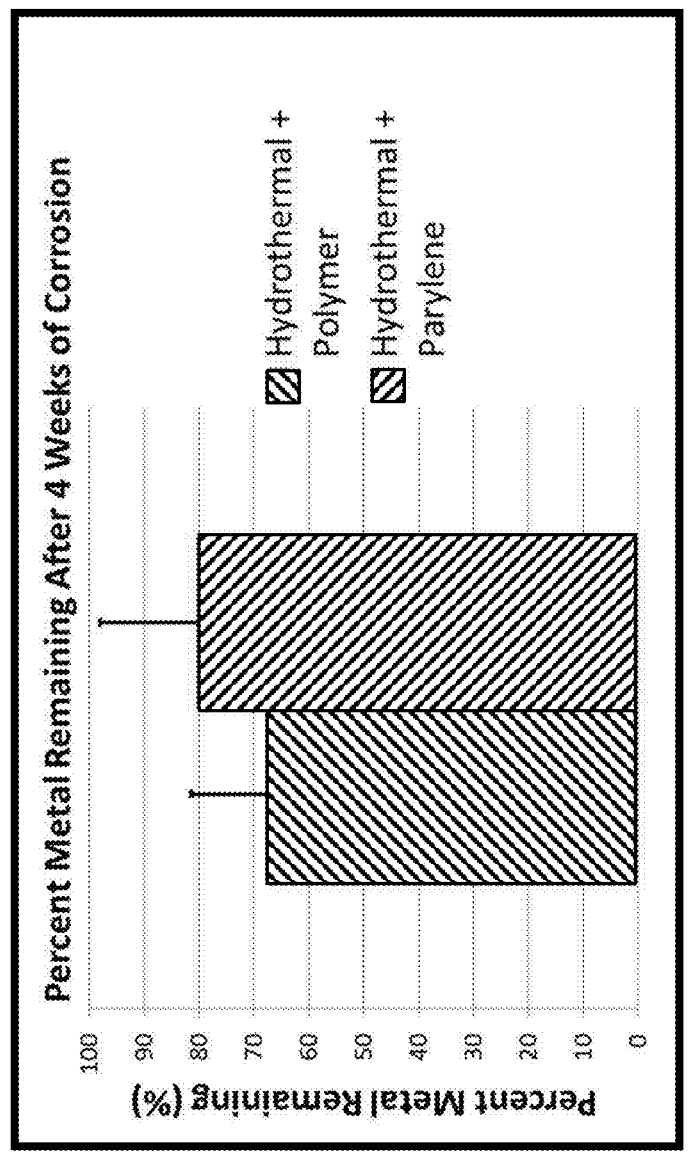
FIG. 5 is a graph illustrating an amount of metal remaining in stents according to embodiments of the invention, after being exposed to a corrosive environment for four weeks.

After the hydrothermal conversion films have been formed on the stent bodies, the stent bodies may then be dipped in or spray-coated with a biodegradable polymer, such as polylactide (pLA), poly(lactide-co-caprolactone), poly(DL-lactide-co-caprolactone), poly(trimethylene carbonate), their copolymers, etc., or a non-biodegradable polymer, such as parylene, polymethacrylates, polyurethane, etc. For example, FIG. 5 illustrates quantitative SEM analysis results for a stent body coated with a hydrothermal conversion film and a parylene coating versus a stent body coated with a hydrothermal conversion film and a poly(DL-lactide-co-caprolactone) coating. The samples were crimped, deployed, and corroded for 4 weeks. Three cross-sections per stent were taken and an image of each strut was taken with SEM. The images were analyzed with Image Pro Plus software to determine the percent metal that remained after 4 weeks of corrosion. As illustrated, even after 4 weeks of corrosion, over 65% of the metal in the stent body remained for the sample that included the hydrothermal conversion film and a poly(DL-lactide-co-caprolactone) coating, and about 80% of the metal in the stent body remained for the sample that included a hydrothermal conversion film and a parylene coating.

In an embodiment, a biodegradable atomic layer deposition (ALD) coating that includes alternating alumina-zircol or zirconia-zircol nanolaminates, or zircol nanolaminates alone, may be applied to the hydrothermal conversion film. In an embodiment, the stent bodies having the hydrothermal film may also be treated with an ALD coating, followed by a polymer overcoat.

It has been found that the combination of these overcoat treatments, i.e. the formation of a hydrothermal conversion film and a coating over the hydrothermal conversion film, has been found to be effective at delaying the corrosion of magnesium alloy (AE42) even after crimping the stent and deploying the stent. The overcoat layer may cover any cracks that have formed in the hydrothermal film so that the stent body is shielded from the external environment, thereby slowing corrosion.

Figure 6:
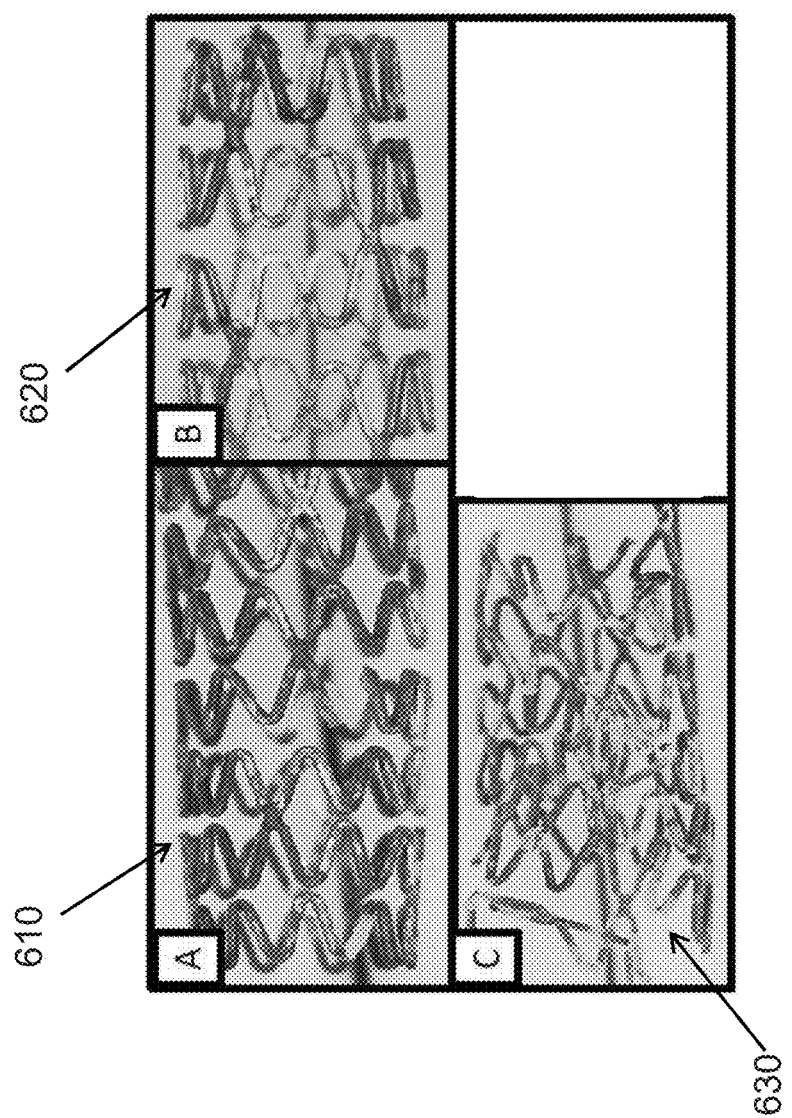
FIGS. 6A-6C illustrate corroded samples of stents with various combinations of coatings that are not in accordance with embodiments of the invention.

It has been found that the individual film coatings are ineffective when used alone on the magnesium alloy stent body, but when used in conjunction with each other, corrosion has been delayed for weeks to months. For example, FIGS. 6A, 6B, and 6C each illustrate a corroded stent body comprised of AE42 magnesium alloy with various combinations of coatings that do not include hydrothermal conversion films. For example, FIG. 6A illustrates a stent body 610 coated with a coating that includes parylene and a coating that includes a poly(lactide-co-caprolactone) copolymer, after the stent body had been exposed to a corrosive environment for 21 days. FIG. 6B illustrates a stent body 620 with a coating that includes parylene, after the stent body had been exposed to a corrosive environment for 96 hours. FIG. 6C illustrates a stent body 630 that was anodized and coated with a coating that includes a poly(lactide-co-caprolactone) copolymer, after the stent body had been exposed to a corrosive environment for 2 weeks. FIGS. 6A-6C illustrate that the coatings used for the stent bodies 610, 620, 630 that were not initially coated with a hydrothermal film were ineffective to delay corrosion by an acceptable amount of time.

Figure 7:
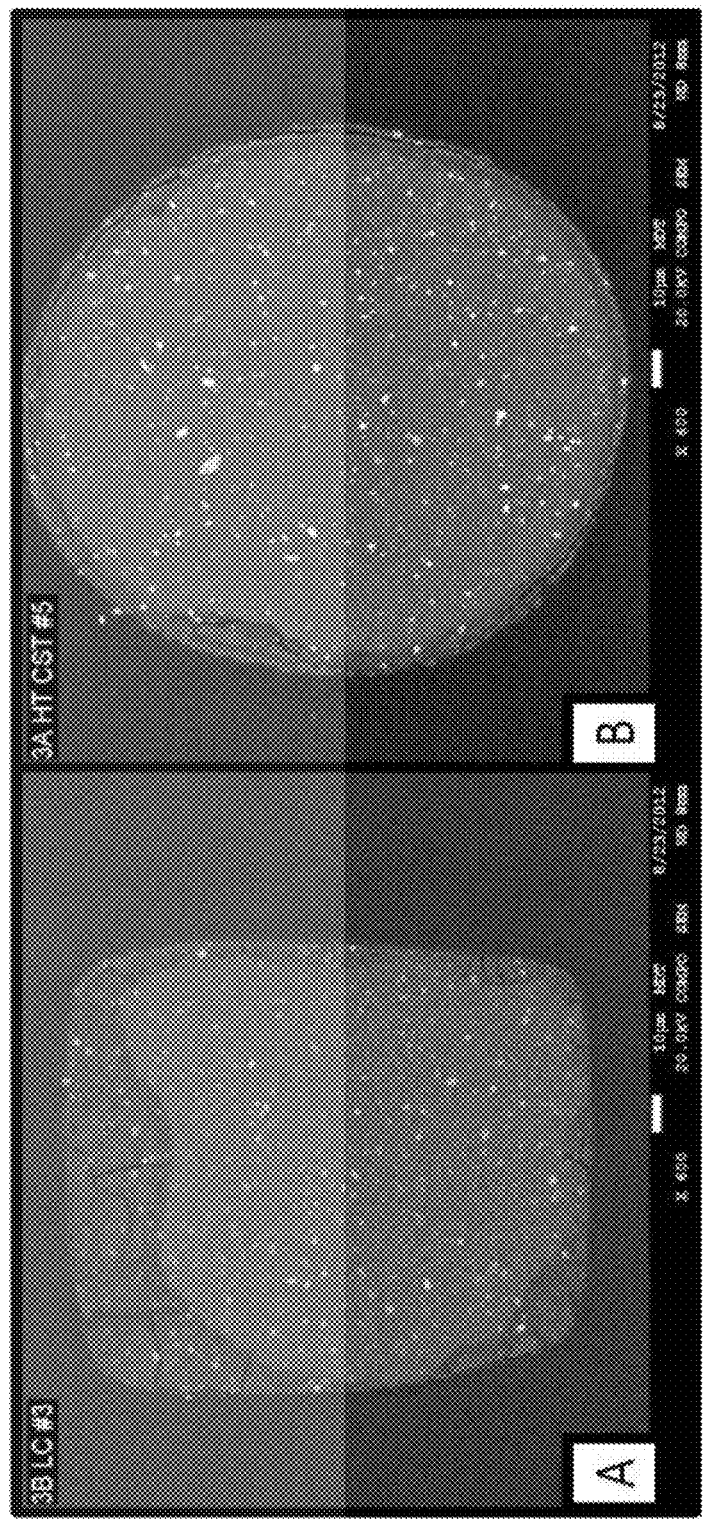
FIG. 7A is a cross-section of a biodegradable atomic layer deposition (ALD) coating on a stent body, after being exposed to a corrosive environment for two weeks.
FIG. 7B is a cross-section showing a hydrothermal conversion film on a stent body, and the ALD coating on the hydrothermal conversion film in accordance with an embodiment of the invention, after being exposed to a corrosive environment for two weeks.

As another example, FIG. 7A illustrates a cross-section of a stent having an ALD coating comprising alumina-zircol nanolaminates directly on the stent body, after being exposed to a corrosive environment for 2 weeks. In contrast, FIG. 7B illustrates a cross-section of a stent having a hydrothermal conversion film on the stent body and an ALD coating comprising alumina-zircol nanolaminates on the hydrothermal conversion film covering the stent body, after being exposed to a corrosive environment for 2 weeks. As illustrated, the stent having both the hydrothermal conversion film and the ALD coating more effectively delayed corrosion at the 2-week time point.

Figure 8:
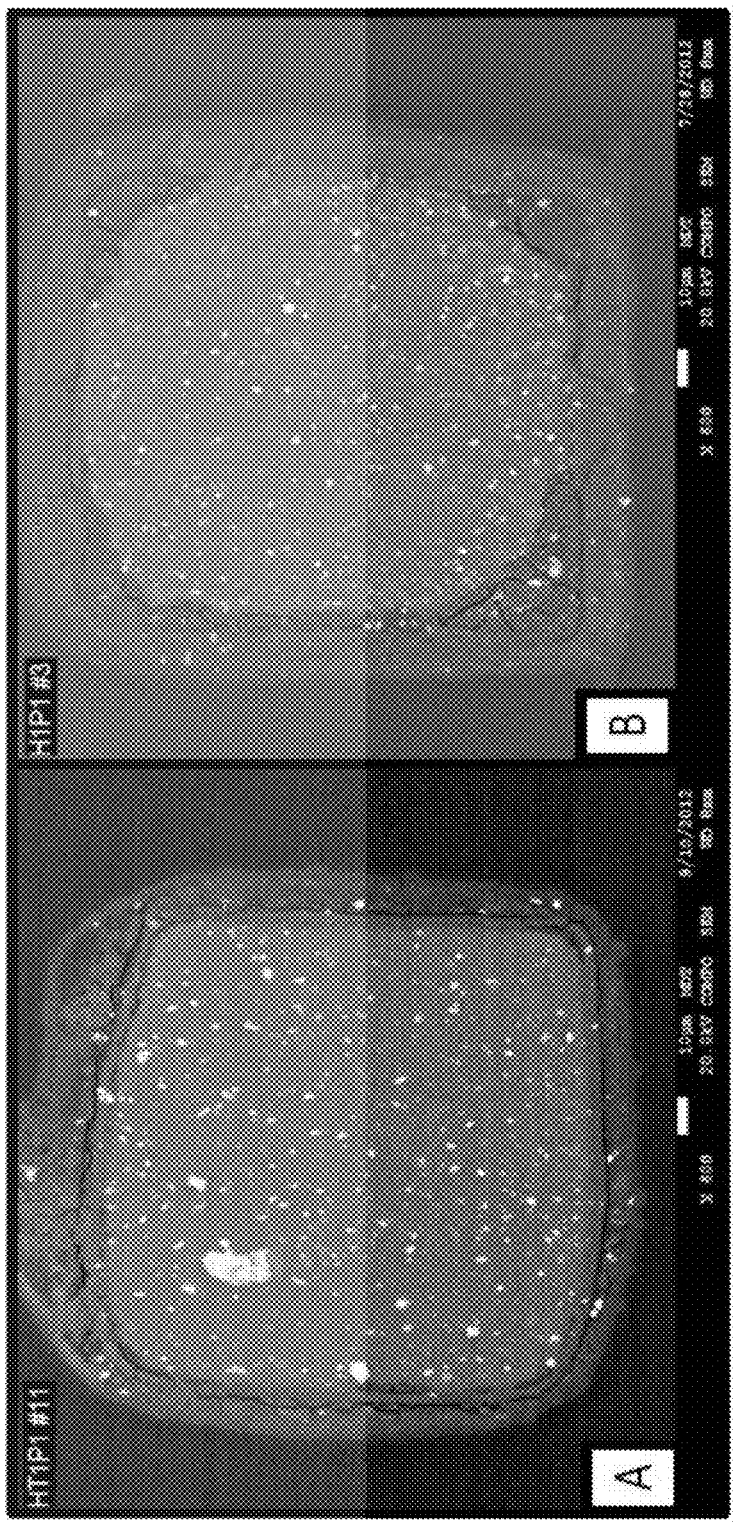
FIG. 8A is a cross-section of a deployed stent in accordance with an embodiment of the invention after 81 days in a corrosive environment.
FIG. 8B is a cross-section of an undeployed stent in accordance with an embodiment of the invention after 126 days in a corrosive environment.

As another example of the effectiveness of coating the stent body with both a hydrothermal film and a parylene coating, FIG. 8A illustrates a cross-section of a deployed stent having a stent body comprising AE42, a hydrothermal conversion film encapsulating the stent body, and a parylene coating encapsulating the stent body coated with the hydrothermal conversion film after being exposed to a corrosive environment for 81 days. FIG. 8B illustrates a cross-section of an undeployed stent having a stent body comprising AE42, a hydrothermal conversion film encapsulating the stent body, and a parylene coating encapsulating the stent body coated with the hydrothermal conversion film after being exposed to a corrosive environment for 126 days. As illustrated a significant amount of the AE42 alloy in the stent body remains.

It has been found that the combination of magnesium oxide conversion films with a secondary layer provides a method for slowing and/or delaying corrosion of the stents. Completely preventing corrosion is not desired, as the stents do need to degrade within, for example, one year. Slow, uniform corrosion is desirable, and focal corrosion is undesirable.

Hydrothermal films have demonstrated to be ineffective at slowing corrosion when used alone on stent bodies. Similarly, polymers (degradable and nondegradable or stable) and atomic layer deposition (ALD) options have also demonstrated to be ineffective when used alone on stent bodies. In addition, it has been found that the combinations of polymer and parylene coatings, and anodization and a polymer coating are not effective options, as corrosion starts in less than 26 days.

As described above, embodiments of the invention provide a combination of a hydrothermal conversion film with a secondary overcoat in order to achieve uniform, slow corrosion, which may enable a bioabsorbable stent to maintain mechanical integrity for 3-6 months, and degrade completely within a year. Other combinations of treatments have not been found to be successful in slowing corrosion to an acceptable level for stent applications, but combinations with a base hydrothermal layer have been found to be effective. For example, when hydrothermal films are used in combination with parylene, stents can last for over 126 days in a corrosive environment. A combination of a degradable polymer and ALD has also showed extended corrosion prevention, as compared to hydrothermal films and coatings by themselves, as well as a more uniform corrosion.

While specific embodiments of the invention have been described above, it will be appreciated that the invention may be practiced otherwise than as described. The descriptions above are intended to be illustrative, not limiting. For example, although the alloys and coatings are described as being used to make a stent, it should be appreciated that other medical devices may also be fabricated with such alloys and coatings in accordance with embodiments of the invention. In addition, although AE42 was the alloy that was used to manufacture stents in accordance with embodiments of the invention, other alloys, particularly magnesium alloys, may be used. It will be apparent to one skilled in the art that modifications may be made to the invention as described without departing from the scope of the claims set out below.

What is claimed is:
1. A stent comprising:
a bioabsorbable metal;
a first coating covering the bioabsorbable metal; and
a second coating covering the first coating, wherein the second coating comprises a biodegradable atomic layer deposition coating, wherein the biodegradable atomic layer deposition coating comprises zircol nanolaminates, alternating alumina-zircol nanolaminates, or alternating zirconia-zircol nanolaminates.
2. The stent according to claim 1, wherein the bioabsorbable metal comprises a magnesium alloy.
3. The stent according to claim 2, wherein the magnesium alloy comprises 90-98 weight % magnesium, 0-6 weight % aluminum, 0-2 weight % zinc, and 0-3% rare earth metal.
4. The stent according to claim 2, wherein the first coating comprises at least one component selected from the group consisting of: magnesium hydroxide and magnesium oxide.
5. The stent according to claim 1, wherein the second coating comprises a non-biodegradable polymer.
6. The stent according to claim 5, wherein the non-biodegradable polymer is selected from the group consisting of: parylene, polymethacrylates, and polyurethane.
7. The stent according to claim 1, wherein the second coating comprises a biodegradable polymer.
8. The stent according to claim 7, wherein the biodegradable polymer is a homopolymer or a copolymer comprising polylactide, poly(lactide-co-caprolactone), poly(DL-lactide-co-caprolactone), or poly(trimethylene carbonate).
9. The stent according to claim 1, wherein the first coating encapsulates the bioabsorbable metal.
10. The stent according to claim 1, wherein the second coating encapsulates the first coating and the bioabsorbable metal.
11. The stent according to claim 1, wherein the second coating comprises a therapeutic substance.
12. The stent according to claim 1, wherein the first coating is a hydrothermal conversion film.
13. A method for manufacturing a stent, the method comprising:
forming a stent body comprising a bioabsorbable metal;
forming a first coating over surfaces of the stent body; and
coating the first coating with a second coating, wherein the second coating comprises a biodegradable atomic layer deposition coating, wherein the biodegradable atomic layer deposition coating comprises zircol nanolaminates, alternating alumina-zircol nanolaminates, or alternating zirconia-zircol nanolaminates.
14. The method according to claim 13, wherein the bioabsorbable metal comprises a magnesium alloy.

15. The method according to claim 14, wherein the magnesium alloy comprises 90-98 weight % magnesium, 0-6 weight % aluminum, 0-2 weight % zinc, and 0-3% rare earth metal.

16. The method according to claim 14, wherein the first coating comprises at least one component selected from the group consisting of magnesium hydroxide and magnesium oxide.

17. The method according to claim 13, further comprising coating the second coating with an overcoat.

18. The method according to claim 17, wherein the overcoat comprises a non-biodegradable polymer.

19. The method according to claim 18, wherein the non-biodegradable polymer is selected from the group consisting of: parylene, polymethacrylates, and polyurethane.

20. The method according to claim 17, wherein the overcoat comprises a biodegradable polymer.

21. The method according to claim 20, wherein the biodegradable polymer is a homopolymer or a copolymer comprising polylactide, poly(lactide-co-caprolactone), poly(DL-lactide-co-caprolactone), or poly(trimethylene carbonate).

22. The method according to claim 17, wherein the overcoat comprises a therapeutic substance.

23. The method according to claim 13, wherein forming the first coating is prepared by a hydrothermal process.

24. A stent comprising:
   a bioabsorbable metal;
   a hydrothermal conversion film covering the bioabsorbable metal; and
   a coating covering the hydrothermal conversion film, wherein the coating comprises a biodegradable atomic layer deposition coating.

* * * * *